United States Patent [19]

Merger et al.

[11] 4,349,484
[45] Sep. 14, 1982

[54] PROCESS FOR THE MANUFACTURE OF MIXTURES OF DIPHENYLMETHANE DIISOCYANATES AND POLYPHENYL POLYMETHYLENE POLYISOCYANATES

[75] Inventors: Franz Merger, Frankenthal; Gerhard Nestler; Friedrich Towae, both of Ludwigshafen; Wolfgang Harder, Weinheim, all of Fed. Rep. of Germany

[73] Assignee: BASF Aktiengesellschaft, Ludwigshafen, Fed. Rep. of Germany

[21] Appl. No.: 197,890

[22] Filed: Oct. 17, 1980

[51] Int. Cl.³ .......................................... C07C 119/048
[52] U.S. Cl. ................. 260/453 P; 252/182; 260/453 AM; 260/453 AR
[58] Field of Search ............... 252/182; 260/453 P, 260/453 AM, 453 AR

[56] References Cited

U.S. PATENT DOCUMENTS

| B 518,076 | 3/1976 | Pistor et al. | 260/453 AM |
|---|---|---|---|
| 4,014,914 | 3/1977 | Pistor et al. | 260/453 AM |
| 4,031,026 | 6/1977 | Ibbotson | 260/453 AM |
| 4,118,410 | 10/1978 | Friedel et al. | 260/453 AM |

FOREIGN PATENT DOCUMENTS

| 2356828 | 5/1975 | Fed. Rep. of Germany | 260/453 AM |
|---|---|---|---|
| 1398975 | 6/1975 | United Kingdom | 260/453 AM |

*Primary Examiner*—Irwin Gluck
*Attorney, Agent, or Firm*—David L. Hedden; Joseph D. Michaels

[57] ABSTRACT

A process for the production of mixtures of diphenylmethane diisocyanates and polyphenyl polymethylene polyisocyanates comprising the steps of A. reacting aniline and an O-alkyl carbamate to form N-phenylurethanes;
B. isolating the N-phenylurethanes;
C. condensing, in the presence of an acid, the N-phenylurethanes with formaldehyde or bifunctional compounds having the formula

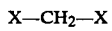

in which X stands for a RO—, RS— or ROCO radical and R denotes an alkyl radical, to form mixtures of methylene bis(phenylurethanes) and polymethylene polyphenylurethanes;
D. cleaving the mixtures of methylene bis(phenylurethanes) and polymethylene polyphenylurethanes at temperatures of 175° C. to 600° C.; and
E. isolating the mixtures of diphenylmethane diisocyanates and polyphenyl polymethylene polyisocyanate resulting from step D.

11 Claims, No Drawings

PROCESS FOR THE MANUFACTURE OF MIXTURES OF DIPHENYLMETHANE DIISOCYANATES AND POLYPHENYL POLYMETHYLENE POLYISOCYANATES

BACKGROUND OF THE INVENTION

1. Field of the Invention

The subject matter of this invention pertains to the preparation of mixtures of diphenylmethane diisocyanates and polymethylene polyisocyanates (hereinafter referred to as crude MDI). Crude MDI is prepared in accordance with this invention by reacting aniline and an O-alkyl carbamate, preferably in the presence of urea and an alcohol, to form N-phenylurethane. The N-phenylurethane is condensed with formaldehyde or various other compounds to form methylene bis(phenylurethane) and polymethylene polyphenylurethane (hereinafter referred to as crude MDU) which is thermally cleaved to form crude MDI.

2. Description of the Prior Art

It is known that crude MDI can be prepared by reacting diphenylmethane diamines and polyphenyl polymethylene polyamines (hereinafter referred to as crude MDA) with phosgene to form corresponding carbamic acid chlorides which can be thermally cleaved into crude MDI. This process is expensive and potentially dangerous because phosgene is toxic and it, along with the carbamic acid chlorides, produces hydrogen chloride which is highly corrosive.

The crude MDA for the process is produced by the condensation of aniline with formaldehyde in the presence of acid catalysts. See British Pat. No. 648,787 and Canadian Pat. No. 700,026. On an industrial scale, hydrogen chloride is added in large quantities. The hydrogen chloride must be neutralized and separated from the reaction mixture.

Because of the problems associated with using phosgene, efforts have been made to develop processes for producing crude MDI without using it. For example, British Pat. No. 1,025,436, German Published Application No. 1,815,517 (U.S. Pat. No. 3,576,835), and German Published Application No. 1,931,212 (U.S. Pat. Nos. 3,654,279 and 3,781,321) describe the preparation of isocyanates by the reaction of nitroaromatics and carbon monoxide. The problems with such processes are that they are technically complicated and cannot be used to produce crude MDI because there is no suitable method for preparing polynitro-polyphenylmethane.

It has been suggested that isocyanates can be prepared by thermally cleaving urethanes. In attempting to accomplish this, several methods of preparing the urethanes have been tried. According to German Pat. No. 1,042,891 (U.S. Pat. No. 2,946,768), a synthesis of crude MDU is possible by means of condensation of phenylurethane with formaldehyde. However, the described process did not result in an industrial scale success because the manufacture of phenylurethane requires the reaction of aniline with chlorocarbonates and/or phenylisocyanate with alcohol. Consequently, the use of phosgene and the problems it creates were not eliminated. Moreover, the condensation product of urethane and formaldehyde contain hydrolysis products with free amino groups and considerable amounts (15 to 50 percent) of N—C bonded components which cannot be cleaved into crude MDI.

A chlorine-free process for the manufacture of phenylurethanes by reacting aniline, urea and alcohol is described in U.S. Pat. No. 2,409,712, and U.S. Pat. No. 2,806,051. However, this process was not successful due to the relatively modest yields in comparison with the phosgenation of aniline and subsequent reaction with alcohol. Therefore, it has not been mentioned in processes for the urethane manufacture described in later publications.

A process for the manufacture of N-substituted urethanes, for instance, phenylurethane, is described in German Published Application No. 2,160,111 (U.S. Pat. No. 3,763,217). The urethanes are prepared by reacting an organic carbonate with aniline in the presence of a Lewis acid. The drawback of this process is the fact that alkylcarbonates must be produced from phosgene and alcohol, or by the technically and still problematic, catalytic cooxidation of carbon monoxide and alcohol, which is expensive. Moreover, the rate of reaction is rather slow and N-alkyl anilines are competing products.

British Pat. No. 1,247,451 describes the preparation of aryl urethanes without using phosgene by reacting nitroaromatics, alcohol, and carbon monoxide. The arylurethanes can be transformed into isocyanates with greater chances of success.

According to data in German Published Application No. 1,568,044 (U.S. Pat. No. 3,467,694), urethanes are produced by reaction of organic nitro compounds, carbon monoxide and hydroxyl-containing compounds in the presence of a catalyst, which consists of a noble metal and a Lewis acid. The reaction occurs under essentially anhydrous conditions in the absence of hydrogen, under increased pressure, and at temperatures above 150° C. According to German Published Application No. 2,343,826 (U.S. Pat. No. 3,895,054), urethanes are obtained from hydroxyl group containing compounds, carbon monoxide and nitro, nitroso, azo and azoxy group containing compounds in the presence of sulfur, selinium, a sulfur and/or selinium compound, and at least one base and/or water. German Published Application No. 2,623,694 (U.S. Pat. No. 4,080,365) describes the manufacture of aromatic urethanes in the presence of selinium containing catalyst systems as well as special aromatic amino and urea compounds.

However, the aforementioned processes also have serious drawbacks. They employ toxic carbon monoxide and catalysts which are toxic or which form toxic compounds during the reaction, such as hydrogen selenide or hydrogen sulfide, or they employ catalysts which are very expensive and are difficult to recycle, such as palladium. They also require high technical expenditure and expensive safety measures.

As was previously mentioned, N-phenylurethane can be condensed with formaldehyde to form crude MDU which can be thermally cleaved to crude MDI. See German Pat. No. 1,042,891. However, according to German Published Application No. 2,832,379, a better form of crude MDU is produced if water is removed from the obtained condensate and if the product is treated with acids in order to complete the transposition of N—C— to C—C— bonded products. Nevertheless, the use of large acid quantities and the formation of resultant byproducts, for instance amines, create a considerable load on the waste water. Therefore, the improved product quality of the crude MDI, according to German Published Application No. 2,832,379, must be obtained by additional increased technical expenditure.

As already mentioned, N-substituted urethanes can subsequently be cleaved thermally into isocyanates. However, there are many problems involved in the cleaving process. The thermal cleaving is accompanied by various undesired secondary reactions. These include, for instance, the decarboxylation reaction of the urethanes which can be accompanied by the formation of primary and secondary amines.

Problems arise regardless of whether the cleaving is done in the vapor phase, liquid phase, or solid phase. According to German Published Application No. 1,944,719 (British Pat. No. 1,247,451), cleaving of the urethanes in the vapor phase is carried out at temperatures of 400° C. to 600° C. in the presence of a Lewis acid as catalyst with the isocyanate and the alcohol being separated by fractional condensation. Vapor phase, in this case, is defined in such a manner that the product mixture, possibly including the solvent, are present in the vapor phase after the cleaving regardless of whether the urethanes to be cleaved are added in the gaseous, liquid, or solid form.

Toluene diisocyanate is produced, for instance, by means of the cleaving of toluene-2,4-diethylurethane in the presence of iron-(III)-chloride. Drawbacks of this reaction include low yields combined with considerable quantities of a polymeric byproduct, and the decomposition and corrosiveness of the catalyst. German Published Application No. 2,410,505 (U.S. Pat. No. 3,870,739) describes a process by which the urethane is cleaved at a temperature of 350° C. to 550° C. and a pressure of less than the (m + 1) times the vapor pressure of the isocyanate product in a catalyst-free pyrolysis zone within 15 seconds. Drawbacks of this process include the fact that a large amount of heat required for the endothermal cleaving must be fed to the powdery urethane within a very short period of time and that a solid polymer, which is incurred as a byproduct, separates. This makes the implementation of a continuous process difficult.

The thermal cleaving of urethanes in the liquid phase is described in German Application No. 2,421,503 (U.S. Pat. No. 3,962,302) and 2,530,001 (U.S. Pat. No. 3,919,280). According to German Application No. 2,421,503, the urethanes are dissolved in an inert solvent such as alkylbenzenes, linear and cyclic hydrocarbons, and/or phthalates, and are cleaved under normal or excess pressure at temperatures of 175° C. to 350° C. The resultant isocyanate and alcohol are isolated and separated with the aid of the solvent as carrier and/or by using an inert gas as a carrier. According to German Application No. 2,530,001, higher molecular, possibly substituted aliphatic, cycloaliphatic or aromatic hydrocarbons, ethers, esters, or ketones, are used as the reaction medium. For separating the cleaved products, this application only cites distillation with isocyanate, alcohol and carrier material being distilled overhead, while the reaction medium remains as bottom fraction.

Some of these drawbacks can be eliminated by using the process described in German Published Application No. 2,635,490. This patent describes a process for preparing aromatic isocyanates wherein the urethanes are brought into contact with a solution of at least one metal ion such as ions of copper, zinc, aluminum, tin, titanium, vanadium, iron, cobalt and nickel as catalysts. The catalysts are dissolved in an inert solvent having a boiling point of 200° C. and are used in a concentration of at least 0.001 percent by weight relative to the solvent. The reaction occurs at temperatures of 150° C. to 350° C. under reduced pressure. The resultant cleaved products are separated by fractional condensation. In some cases, this method is successful in converting urethanes into isocyanates with good yields. However, it is noteworthy that the manufacture of crude MDI is not described by example in this patent. The reason is that crude MDI cannot be completely distilled with the aid of solvents as carrier materials and, therefore, can not be isolated from the catalyst, possibly unreacted raw materials, and byproducts.

SUMMARY OF THE INVENTION

Applicants have discovered a process for the manufacture of mixtures of diphenylmethane diisocyanates and polyphenyl polymethylene polyisocyanates (crude MDI) comprising the steps of A. reacting aniline with an O-alkylcarbamate to form N-phenylurethane;

B. isolating the N-phenylurethane;

C. condensing, in the presence of an acid, the N-phenylurethane with formaldehyde or bifunctional compounds having the formula $$X-CH_2X$$

in which X stands for a RO—, RS—, or ROCO— radical and R denotes an alkyl radical, to form mixtures of methylene bis(phenylurethanes) and polymethylene polyphenylurethanes (crude MDU);

D. cleaving the mixtures of methylene bis(phenylurethanes) and polymethylene polyphenylurethanes at temperatures of 175° C. to 600° C.; and E. isolating the mixture of diphenylmethane diisocyanate and polyphenyl polymethylene polyisocyanates resulting from step D.

The process according to this invention can be illustrated schematically by equations (I) to (IV).

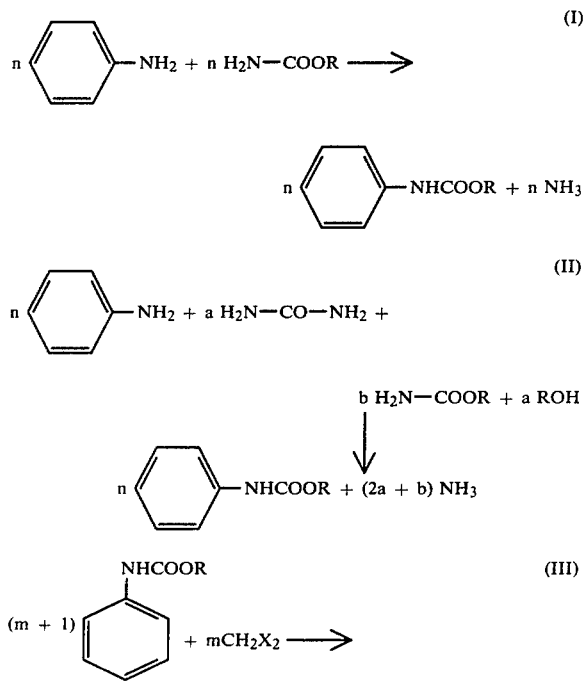

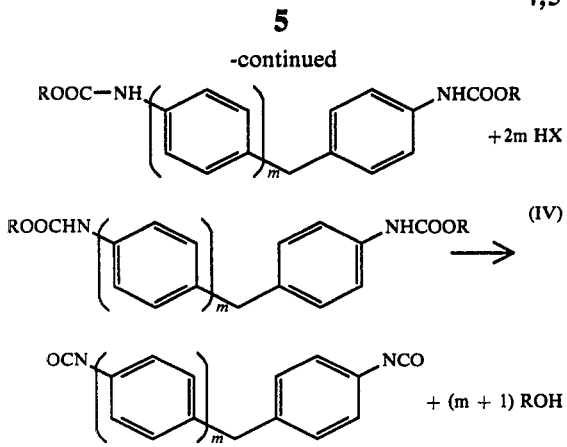

In equations (I), (II), (III) and (IV), n, a, b and m stand for whole numbers with $a+b=n$ and $a:n=1.5$ to 0 according to equation (II), and in which $m=1$ to 6 and greater in accordance with equations (III) and (IV).

The formation of N-phenylurethane in one process stage and in good yields is surprising. According to familiar teachings, carbamates and aromatic amines result in N,N'diarylureas which are usually transcrystalized from alcohol. It is also known that non-substituted urethanes, in the presence of aromatic amines, continue to react very easily to form N,N'-diarylureas in the presence of alcohol. Houben-Weyl, *Methods of Organic Chemistry*, Vol. 8, pages 152, 140, and 161 (Georg Thieme Publishers, Stuttgart, 1952).

It is also surprising that, in accordance with this invention, N-phenylurethane can be produced catalytically from aniline and O-alkylcarbamates even in the absence of alcohol; that excess O-alkylcarbamates do not result in considerable decomposition and polycondensation; that the reaction can be implemented on a large scale and can be improved in its selectivity by adding certain catalysts in lower temperatures; and that the reaction with urea and alcohol in the presence of certain catalysts becomes considerably more effective on a large scale even at lower temperatures if it is carried out with larger quantities of O-alkylcarbamates.

Finally, it is surprising that the resultant N-phenylurethane can be transformed into crude MDU without difficulties in good yields, with a high degree of purity, and in the absence of water, particularly with acetals and acylals having the formulas $CH_2(OR)_2$ and $CH_2(OCOR)_2$.

DESCRIPTION OF THE PREFERRED EMBODIMENTS

In order to prepare crude MDI in accordance with this invention, N-phenylurethane is condensed with formaldehyde or various other compounds to form crude MDU which is thermally cleaved to produce crude MDI. The N-phenylurethane is first prepared by the reaction of aniline, O-alkyl carbamates, and preferably urea and alcohol. A complete description of the process for preparing N-phenylurethanes will first be described. Then the preparation of crude MDU from the N-phenylurethane will be described. Finally, the preparation of crude MDI from crude MDU will be described.

For the preparation of N-phenylurethanes, an O-alkyl carbamate is reacted with aniline. Suitable O-alkylcarbamates have the formula $H_2N-COOR$ in which R represents a substituted or unsubstituted aliphatic, cycloaliphatic or aromatic radical. Suitable examples include O-alkylcarbamates based on primary aliphatic monoalcohols having 1 to 20 carbon atoms, preferably 1 to 10 carbon atoms, such as methyl carbamate, ethyl carbamate, propyl carbamate, n-butyl carbamate, isobutyl carbamate, 2- and 3-methylbutyl carbamate, neopentyl carbamate, pentyl carbamate, 2-methylpentyl carbamate, n-hexyl carbamate, 2-ethylhexyl carbamate, heptyl carbamate, n-octyl carbamate, n-nonyl carbamate, n-decyl carbamate, and n-dodecyl carbamate, 2-phenylpropyl carbamate; O-alkylcarbamate based on secondary aliphatic and cycloaliphatic monoalcohols having 3 to 15 carbon atoms, preferably 3 to 6 carbon atoms, such as isopropyl carbamate, secondary butyl carbamate, secondary isoamyl carbamate, cyclopentyl carbamate, cyclohexyl carbamate, bicyclo(2,2,1)-heptyl carbamate, and tertiary butylcyclohexylhexyl carbamate. Preferably used are methyl carbamate, ethyl carbamate, butyl carbamate, isobutyl carbamate, 2- and 3-methylbutyl carbamate, pentyl carbamate, hexyl carbamate, 2-ethylhexyl carbamate, heptyl carbamate, octyl carbamate, and cyclohexyl carbamate.

As was previously mentioned, the reaction of the O-alkyl carbamates and aniline preferably is carried out in the presence of alcohols and urea. Urea is appropriately used in its commercially available form and purity.

Suitable alcohols include unsubstitited and substituted, primary or secondary aliphatic alcohols as well as mixtures thereof. Preferably used is the alcohol which has an alkyl group corresponding with the alkyl group of the O-alkylcarbamates. Representative examples include primary aliphatic alcohols having 1 to 20 carbon atoms, preferably 1 to 10 carbon atoms, such as methanol, ethanol, propanol, n-butanol, n-pentanol, neopentylalcohol, 2-methylbutanol, 2-methylpentanol, n-hexanol, n-heptanol, n-octanol, nonanol, n-decanol, and n-dodecanol; secondary aliphatic and cycloaliphatic alcohols having 3 to 15 carbon atoms, preferably 3 to 6 carbon atoms such as isopropanol, secondary butanol, secondary isoamyl alcohol, cyclopentanol, 2-, 3- or 4-methylcyclohexanol, cyclohexanol and bicyclo(2,2,1)-heptanol. Preferably used as monoalcohols are methanol, ethanol, propanol, isopropanol, n-butanol, 2-ethylbutanol, 2- and 3-methylbutanol, n-pentanol, n-hexanol, 2-ethylhexanol, heptanol, octanol and cyclohexanol. The alcohols may possibly be mixed with other organic solvents which are inert under the reaction conditions.

For the manufacture of the N-phenylurethanes in the absence of catalysts, the aniline, O-alkylcarbamate and alcohol are reacted in a mole ratio of 1 to 0.5:10 to 0:100, preferably 1 to 0.8:10 to 1:50 and particularly 1 to 1:6 to 1:5. However, if the reaction takes place in the presence of catalysts, mole ratios of aniline to O-alkylcarbamates to alcohol of 1 to 0.5:20 to 0:100, preferably 1 to 0.8:10 to 0:30, and particularly 1 to 1:6 to 0:5, have proven to work particularly well. If urea is also used, the mole ratio of aniline to the sum of O-alkylcarbamate and urea is also 1 to 0.5:20, preferably 1 to 0.8:10 and particularly 1 to 1:6, with the mole ratio of urea to aniline being equal to or less than 1.5, preferably 1.25 to 0.75 and a mole ratio of urea to alcohol being equal to or less than 1.

It is not necessary to produce the O-alkylcarbamates separately. According to an easily implemented, preferably used version, the O-alkylcarbamate is used together with urea and alcohol and, after extensive to complete reaction of the aniline, is separated by means of distillation and is possibly recycled. The process may also be carried out on a continuous basis.

In order to increase the rate of reaction and to improve the yields, the reaction is preferably carried out in the presence of one or more catalysts. Suitable catalysts include inorganic and organic compounds having one or more, preferably one, cation of metals or groups IA, IB, IIA, IIB, IIIA, IIIB, IVA, IVB, VA, VB, VIB, VIIB and VIIIB of the periodic system defined according to the *Handbook of Chemistry and Physics*, (14th Ediion, published by Chemical Rubber Publishing Company, 2310 Superior Ave. N.E., Cleveland, Ohio). The compounds, for instance, include halides such as chlorides and bromides, sulfates, phosphates, nitrates, borates, alcoholates, phenylates, sulfonates, oxides, oxide hydrates, hydroxides, carboxylates, chelates, carbonates, and thio or dithiocarbamates. The compounds may include the cations of the following metals: lithium, sodium, potassium, magnesium, calcium, aluminum, gallium, tin, lead, bismuth, antimony, copper, silver, gold, zinc, mercury, cerium, titanium, vanadium, chrome, molybdenum, manganese, iron, cobalt and nickel. Preferably used are the cations of lithium, calcium, aluminum, tin, bismuth, antimony, copper, zinc, titanium, vanadium, chrome, molybdenum, manganese, iron and cobalt. Without recognizable marked drawbacks, these catalysts may also be used in the form of their hydrates or ammoniaates.

Representative examples of typical catalyst include the following compounds: lithium methanolate, lithium ethanolate, lithium propanolate, lithium butanolate, sodium methanolate, potassium-tertiary butanolate, magnesium methanolate, calcium methanolate, tin-(II)-chloride, tin-(IV)chloride, lead acetate, lead phosphate, antimony-(III)chloride, antimony-(V)-chloride, aluminum isobutylate, aluminum trichloride, bismuth-(III)-chloride, copper-(II)acetate, copper-(II)-sulfate, copper-(II)-nitrate, bis(triphenylphosphineoxydo)-copper-(II)-chloride, copper molybdate, silver acetate, gold acetate, zinc oxide, zinc chloride, zinc acetate, zinc acetonylacetate, zinc octoate, zinc oxalate, zinc hexylate, zinc benzoate, zinc undecylate, cerium-(IV)-oxide, uranylacetate, titanium tetrabutanolate, titanium tetrachloride, titanium tetraphenolate, titanium naphthenate, vanadium-(III)-chloride, vanadium acetonylacetate, chrome-(III)-chloride, molybdenum-(VI)-oxide, molybdenum acetylacetonate, tungston-(VI)-oxide, manganese-(II)-chloride, manganese-(II)-acetate, manganese-(III)-acetate, iron-(II)acetate, iron-(III)-acetate, iron phosphate, iron oxylate, iron-(III)-chloride, iron-(III)-bromide, cobalt acetate, cobalt chloride, cobalt sulfate, cobalt naphthanate, nickel chloride, nickel acetate, and nickel naphthenate as well as their mixtures.

The catalysts are advantageously used in quantities corresponding with 0.0001 to 0.1, preferably 0.0005 to 0.05 equivalents of the metal cation, relative to aniline. The metal ions may also be used bonded to ion exchangers in the heterogeneous phase.

The reaction is carried out at increased temperatures, for instance, in the absence of catalysts at temperatures of 160° C. to 300° C., preferably 170° C. to 230° C., and particularly 175° C. to 210° C., and in the presence of catalysts at temperatures of 100° C. to 250° C., preferably 120° C. to 210° C., and particularly 135° C. to 190° C., under pressures of 0.1 to 120 bars, preferably 0.5 to 60 bars, and particularly 1 to 40 bars. It has proven to be advantageous to separate the resulting ammonia from the reaction mixture, for instance, by means of distillation. At a given temperature, the reaction is then preferably carried out under a pressure at which the resulting ammonia can be selectively distilled from the reaction mixture. The corresponding values are contained in tables with physical data for ammonia and alcohol. The reaction times for the referenced temperature ranges are 0.5 to 100 hours, preferably 1 to 50 hours, and particularly 2 to 25 hours.

An advantageous method for preparing the N-phenylurethanes will now be described. Aniline, O-alkylcarbmates, and possibly alcohols and/or urea, are mixed in the above-referenced quantity ratios preferably in the presence of a catalyst. The ingredients are heated in a reaction vessel equipped with a device for separating the ammonia, if required, while being stirred. After the reaction has been completed, the resulting ammonia can be separated. Preferably, however, it is removed by continuous or batch-type distillation during the reaction. Particularly in case of the reaction in the presence of low molecular alcohols under pressure, it may be advantageous to separate the ammonia with the aid of a stripping agent which is inert under the reaction conditions, such as a gas like nitrogen. Subsequently, and if required after separating the catalyst and removing solids by filtration, the N-phenylurethane is isolated from the resultant reaction mixture. This may be accomplished, for instance, by fractional distillation, by distilling the excess O-alkylcarbamate and/or alcohol, by partial distillation of the excess O-alkylcarbamate and/or alcohol and crystallization of the N-phenylurethane, by crystallization, by precipitation with or also by transcrystallization from other solvents. If required, the catalysts may be separated, for instance, by means of sedimentation, filtration, washing, or bonding to ion exchangers.

The next step of the process of this invention concerns the preparation of crude MDU. Crude MDU is prepared by condensing the N-phenylurethane with formaldehyde or preferably compounds having the formula X—$CH_2$—X wherein X represents a RO—, RS— or ROCO radical and in which R stands for an alkyl radical. The condensation is carried out in the presence of an acid.

In accordance with the currrent state of the art, the crude MDU may be produced in two stages by condensation of N-phenylurethane and formaldehyde according to German Pat. No. 1,042,891 and completion of the reaction according to German Published Application No. 2,832,379.

According to the invention, however, the condensation of N-phenylurethane is advantageously carried out in a single stage with formaldehyde or formaldehyde separating compounds, such as trioxane or paraformaldehyde, in a possibly substituted carboxylic acid such as propionic acid, chloroacetic acid, or preferably acetic acid as solvent (according to O.Z. 0050/034092, German Patent Application No. P29 42 137.2 by BASF Aktiengesellschaft). Preferably, the condensation is carried out with bifunctional compounds having the formulas $CH_2(SR)_2$, $CH_2(OR)_2$ or $CH_2(OCOR)_2$, in which R stands for an alkyl radical having 1 to 6, preferably 1 to 3 carbon atoms, in the presence of a strong acid. Under the reaction conditions, the thioacetals, acetals or acylals form essentially no free formaldehyde and prevent the formation of water of reaction. The use of acetals and acylals is of particular technical interest. Preferably used are those compounds of the referenced type in which the alkyl radical corresponds with the alcohols upon which the N-phenylurethane is based. Examples include formaldehyde, dimethylacetal (also known as dimethylformal), diethylformal, and diacetoxymethane. The use of dimethylformal is particularly advantageous since it can be obtained easily and profitably from aqueous formaldehyde and methanol.

The condensation of N-phenylurethane with formaldehyde and carboxylic acid, or with a bifunctional compound in the presence of an acid, is carried out at temperatures from 50° C. to 160° C., preferably 90° C. to 140° C., and particularly 90° C. to 120° C.

The mole ratio of formaldehyde and/or bifunctional compound to N-phenylurethane is generally 1:05 to 1:10, preferably 1:1.5 to 1:3. If one wishes to primarily produce methylene bis(phenylurethane) and largely avoid the formation of methylene polyphenylurethanes, a ratio of 1:4 to 1:8 is preferred. If substituted carboxylic acids are used as solvents, these are used in a quantity of 50 grams to 500 grams, preferably 100 grams to 200 grams, per mole of N-phenylurethane.

Suitable solvents, which for instance are used in quantities of 1 to 100 mole percent, preferably 20 to 60 mole percent, relative to the N-phenylurethane, include phosphoric acid, sulfuric acid, hydrogen chloride, alkylsulfonic acid such as methane sulfonic acid and trifluoromethane sulfonic acid, or arylsulfonic acid such as p-toluene sulfonic acid. According to a particularly advantageous version, a strong acid is used such as methane sulfonic acid and trifluoromethane sulfonic acid, which may be separated from the reaction mixture by distillation. This eliminates processing of the reaction mixture with water or bases and the acid can be directly recycled to the reaction.

According to another advantageous version, strongly acid organic cation exchangers are used as acids such as sulfonic acid exchange resins. Examples include: Lewasorb ® AC-10 (Bayer AG), Lewatit ® SPC-108 (Bayer AG), Amberlyst ®-15 (Rohm and Haas, Co.) or Nafion acid (Dupont de Nemours). These ion exchangers are either suspended in the reaction mixture or arranged in a fixed bed according to basically familiar methods.

The condensation is preferably conducted in the absence of water, that is by using acids, which contain essentially no water. The condensation can be carried out with or without a non-aqueous solvent such as benzene, methylcyclohexane, acetic acid, sulfolan, methanol, methylacetate, nitrobenzene, chlorobenzene, dichlorobenzene, or chlorinated aliphatic hydrocarbons.

The reaction, which is completed after approximately 0.5 to 20 hours, is generally carried out in accordance with one of the two methods listed below. A mixture of paraformaldehyde and carboxylic acid, for instance, or the bifunctional compound is slowly added to a mixture of the N-phenylurethane and the catalyst at the reaction temperature while being stirred; or a mixture of N-phenylurethane, paraformaldehyde and carboxylic acid and/or the bifunctional compound in the catalyst is heated while being stirred; and the mixture is maintained at the reaction temperature for the corresponding period of time. The reaction product is isolated according to traditional methods, for instance, by distillative separation of the solvent and extraction of the catalyst with water or neutralization with a base. If nonreacted raw materials are present, they can be separated by means of vacuum distillation. The condensation of the N-phenylurethanes with formaldehyde and/or the referenced formaldehyde derivates can be carried out by a batch method or as a continuous process.

According to the condensation process of this invention, crude MDU's are obtained which, depending upon the selected mole ratios of N-phenylurethane and formaldehyde and/or bifunctional compound, have methylene bis(phenylurethanes) in quantities of 20 to 90 percent by weight, preferably of 40 to 80 percent by weight, relative to the total weight, and have the following isomer distribution: methylene bis(4-phenylurethane), 70 to 95 percent by weight, preferably 80 to 95 percent by weight; and methylene(2-phenylurethane)-4-phenylurethane, 30 to 5 percent by weight, preferably 5 to 20 percent by weight; in each case relative to the total weight of methylene-bisphenylurethanes.

Under certain circumstances, it may be advantageous to totally or preferably partially separate the methylene-bisphenylurethanes from the crude MDU and separate them into the isomers. This may be done, for instance, by fractional crystallization.

Crude MDI is prepared from the crude MDU by thermal cleaving at temperatures from 175° C. to 600° C. The thermal cleaving may be carried out in the absence of catalysts, for instance, according to German Published Application No. 2,410,505 (U.S. Pat. No. 3,870,739), or in the presence of catalysts, for instance, according to German Published Application No. 1,944,719 (British Pat. No. 1,247,451). Preferably, the thermal cleaving is carried out in the liquid phase in the presence of solvents, free of catalysts, for instance, in accordance with German Application No. 2,421,503 (U.S. Pat. No. 3,962,302) or German Application No. 2,530,001 (U.S. Pat. Nos. 3,919,280 and 3,919,279), or in the presence of solvents and dissolved catalysts, for instance, according to the data in German Published Application No. 2,635,490 at temperatures of 175° C. to 350° C.

Since the removal of dissolved catalysts from the reaction mixtures creates problems, it is recommended that the cleaving take place in the absence of catalysts. Surprisingly, however, it has been shown to be advantageous to accelerate the thermal cleaving by heterogeneous catalysis using metals selected from the group consisting of zinc, aluminum, titanium, iron, chrome, cobalt, and nickel with zinc and aluminum being used on a preferred basis. These metals may be used in combination with other metals such as vanadium and tungsten. The catalysts preferably have a large surface area, for instance in the form of metal powders or granules having average diameters of 2 millimeters to 10 millimeters, metal shavings, or wool. The metals are not only good heat conductors but, in addition to this, they have a technically good catalytic effect. Consequently, the reaction temperatures and/or times are reduced, and secondary reactions, such as polymerizations, are less pronounced.

The catalysts may be used in various arrangements. They can be used as fixed beds, for instance, by charging tube or boiler reactors with metal granules, rings, shavings or wool, so that the reaction mixture can be directed continuously through the fixed catalyst bed. Alternatively, the catalyst may be arranged in suspension in mixing reactors.

Cleaving of the crude MDU is preferably carried out in the liquid phase. In this case, solvents are preferred which are inert with respect to isocyanates and the other components, and the boiling points of which are below the boiling point of 4,4'-diphenylmethane diisocyanate and preferably about that of the alcohol to be cleaved. In addition to this, the critical temperature of the solvent may not be less than 175° C. It is also advantageous if the crude MDU is soluble in the solvent, although this is not absolutely essential. Representative examples of solvents include the following: aliphatic hydrocarbons such as the higher alkanes, decane, undecane, dodecane, tridecane, tetradecane, pentadecane, hexadecane, heptadecane and decaline; possibly subsituted aromatic hydrocarbons such as naphthaline, 1- and 2-methylnaphthalene, 1,2-, 1,4-, 1,6-, 2,7-, 2,6- and 2,3-dimethylnaphthalene, 1-ethylnaphthalene, toluene, 1,2-, 1,3- and 1,4-dimethylbenzene, 1,2,4- and 1,3,5-trimethylbenzene, 1,2,3,5- and 1,2,4,5-tetramethylbenzene, 1,3,5-triethylbenzene, hexyl-, heptyl-, octyl-, nonyl-, decyl- and dodecylbenzene, hexamethylbenzene, hexaethylbenzene, diphenyl, 4,4'-dimethyldiphenyl, dibenzyl, diphenylmethane and 4,4'-dimethyldiphenylmethane; halogen-substituted aromatic hydrocarbons such as chlorobenzene, 1,2- and 1,4-dichlorobenzene, 1,4-diiotobenzene, 1,2,3- and 1,3,5-trichlorobenzene, 1,2,3,4-, 1,2,3,5- and 1,2,4,5-tetrachlorobenzene, pentachlorobenzene, 1- and 2-fluoronaphthalene, 1- and 2-chloronaphthalene, 1- and 2-iotonaphthalene, and diphenyldichloromethane; nitro group-containing aromatic hydrocarbons such as nitrobenzene, 3-nitrotoluene, 2-nitro-m-xylene, 5-nitro-m-xylene, and 4-nitroanisol; aliphatic and aromatic ketones such as cyclohexanone, cycloheptanone, di-n-butylketone, di-n-amylketone, -tetralon acetophenone, propiophenone, benzophenone, 3-methylbenzophenone, dodecanone-2 and tridecanone-2; sulfones and carboxylates such as sulfolane, diethylsulfone, dimethylphthalate, diethylphthalate, propylbenzoate; and ethyllaurate and ethers such as diethylene glycol dimethyl ether, diethylene glycol diethyl ether, diisoamyl ether, di-n-amyl ether, resorcin dimethyl ether, resorcin diethyl ether, phenyloctyl ether, phenylbenzyl ether, dibenzyl ether, diphenyl ether, α-methylnaphthyl ether and β-ethylnaphthyl ether.

Thermal cleaving of crude MDU in the presence of metals is carried out at temperatures of 175° C. to 600° C., preferably in a solvent at 175° C. to 350° C., particularly at 230° C. to 350° C., under reduced, normal or increased pressure by a batch method or preferably on a continuous basis. The products may be cleaved and separated either in sequence or preferably simultaneously. Crude MDU, for instance, molten, as a powder, or as suspension and/or solution, can be introduced into the reactor in an inert solvent. The reactor can be maintained at a chosen temperature and a chosen pressure. For example, the solution of crude MDU may be directed through a cascade which consists alternatingly of tube cleaving reactors and separating columns. According to preferred versions, the solution of the crude MDU corresponding with 0.1 to 5, preferably 0.2 to 3, equivalents of urethane per liter an hour is directed continuously into a reactor and/or a reactor cascade with simultaneous cleaving and separation of the alcohol via one or more separating columns. A temperature/pressure ratio is selected so that the solvent is refluxed or is partially removed by distillation together with the alcohol. Thereafter, the solvent may be removed by careful distillation, possibly by stripping, preferably through evaporators with large surface areas. This will decrease the residence time with diphenylmethane diisocyanates functioning as carrier material. The crude MDI can be removed as a bottom fraction. It has proven to be advantageous to distill and recycle part of the diphenylmethane diisocyanate together with the solvent.

The parts referred to in the examples which follow are relative to weight.

EXAMPLE 1

In a reaction vessel, 93 parts of aniline, 450 parts of methyl carbamate, 0.9 part of iron-(II)-acetate, and 95 parts of methanol are heated to 175° C. to 180° C. for 6 hours with a pressure of 5 bars to 6 bars being maintained in the reaction vessel via a pressure valve. Using 15 liters of nitrogen per liter of reaction mixture an hour as a striping agent, the ammonia formed during the reaction is continuously removed by distillation. After the reaction is completed, unreacted aniline, excess methanol and excess methylcarbamate are removed by distillation at approximately 20 millibars. By distillation at temperatures of 110° C. to 113° C. and 0.1 millibars, 127 parts of N-phenylmethylurethane are obtained (88.5 percent of theory relative to reacted aniline). The distillation residue contains additional N-phenylmethylurethane. By gas chromatography, it was determined that 95 percent of the aniline was reacted.

The N-phenylurethane obtained in this manner is heated in a mixing autoclave together with 32 parts of dimethylformal, 93 parts of nitrobenzene and 17 parts of sulfuric acid to 100° C. while being stirred. The mixture is stirred at this temperature for a period of 10 hours. After completing the reaction and extracting the acid with water, the solvent and unreacted raw materials are removed by distillation under reduced pressure. The result is 126 parts of a distillation residue. According to high pressure liquid chromatography analysis, 52 percent of this residue consists of bis(methoxycarbonylamino)diphenylmethane, 30 percent of 3-nucleus, and 18 percent of higher nucleus polymethylenepolyphenyl urethanes (crude MDU).

The resultant crude MDU is dissolved in 550 parts of sulfolane. It is then pumped employing a feed rate of 300 parts per liter of reaction space an hour into a quartz glass tube reactor filled with zinc shavings and heated to 300° C. The methanol formed by the cleaving process is separated in the gaseous form and is condensed in a receiving vessel cooled with dry ice. Obtained are 658 parts of reactor discharge from which the cleaving solvent, sulfolan, is distilled at 90° C. to 95° C. and 0.1 millibar. The remaining product consists of 112 parts of a mixture of 57 percent diphenylmethane diisocyanates plus 31 percent 3-nucleus and 12 percent higher nucleus polyphenyl polymethylene polyisocyanates.

EXAMPLE 2

In a reaction vessel, 60 parts of aniline, 172 parts of ethyl carbamate, 38 parts of urea, 0.75 part of cobalt acetate, and 90 parts of ethanol are heated to 175° C. to 180° C. for five hours with a pressure of 5 bars to 7 bars being maintained in the reaction vessel via a pressure valve. Using 12 liters of nitrogen per liter of reaction mixture an hour as a stripping agent, the ammonia formed during the reaction is removed by continuous distillation. After the reaction is completed, unreacted aniline, excess ethanol and excess ethyl carbamate are removed by distillation at approximately 12 millibars. By distillation at 123° C. to 126° C. and 0.1 millibar, 89 parts of N-phenylethylurethane are obtained (86.2 percent of theory relative to reacted aniline). The distillation residue contains additional phenylethylurethane.

By gas chromatographically, it is determined that 97 percent of the aniline has reacted.

The N-phenylethylurethane obtained in this manner is heated with 9 parts of paraformaldehyde, 60 parts of acetic acid, and 18 parts of Lewatit SPC-108 to 100° C. while being agitated. It is agitated at this temperature for 10 hours.

After the reaction is completed, the catalyst is removed by filtration and the solvent and unreacted raw materials are removed by distillation under reduced pressure. Obtained are 88 parts of the distillation residue. According to high pressure liquid chromatography analysis, 55 percent of this residue consists of bis(ethoxycarbonylamino)diphenylmethane plus 29 percent 3-nucleus and 16 percent higher nucleus polymethylene polyphenylurethane (crude MDU).

The crude MDU obtained in this manner is dissolved in 500 parts of decylbenzene and is pumped at a feed rate of 300 parts per liter of reaction space an hour into a quartz glass tube reactor filled with aluminum granules and heated to 320° C. The ethanol formed during the cleaving process is separated in the form of gas and is condensed in a receiving vessel filled with dry ice.

Obtained are 545 parts of reactor discharge from which the cleaving solvent, decylbenzene, is distilled at 85° C. to 95° C. at 0.2 millibar. The remaining product consists of 69 parts of a mixture of 58 percent of diphenylmethane diisocyanates plus 29 percent 3-nucleus and 13 percent higher nucleus polyphenyl polymethylene polyisocyanates.

EXAMPLE 3

In a reaction vessel, 93 parts of aniline, 450 parts of methyl carbamate, 0.9 part of iron-(II)-acetate, and 95 parts of methanol are heated to 175° C. to 180° C. for 6 hours with a pressure of 5 bars to 7 bars being maintained in the reaction vessel via a pressure regulation valve. Using 15 liters of nitrogen per liter of reaction mixture an hour as a stripping agent, the ammonia formed during the reaction is removed by continuous distillation. After the reaction has been completed, unreacted aniline, excess methanol and excess methyl carbamate are removed. By distillation at approximately 20 millibar and by distillation at 109° C. to 113° C. and 0.1 millibars, 133 parts of N-phenylmethylurethane (93.7 percent of theory relative to reacted aniline) are obtained. Additional phenylmethylurethane is contained in the distillation residue. It is determined that 94 percent of the aniline has been reacted.

The N-phenylmethylurethane obtained in this manner is heated together with 58 parts of diacetoxymethane, 106 parts of nitrobenzene, and 44 parts of Lewatit SPC-108 to 100° C. in an agitator reactor while being agitated, and is agitated at this temperature for 5 hours. After the reaction has been completed, the catalyst is separated and nitrobenzene and non-reacted raw material is removed by distillation under reduced pressure. Obtained are 125 parts of a distillation residue. According to high pressure liquid chromatography, 76 percent of this residue consists of bis(methoxycarbonylamino)-diphenylmethane plus 16 percent of 3-nucleus and 8 percent of higher nucleus polymethylene polyphenylurethanes (crude MDU).

The crude MDU obtained in this manner is dissolved in 375 parts of decylbenzene and is pumped at a feed rate of 320 parts per liter of reaction mixture an hour into a quartz glass tube reactor filled with zinc shavings and heated to 310° C. The methanol formed by the cleaving process is separated in the gaseous form and is condensed in a receiving vessel cooled with dry ice. Obtained are 472 parts of reaction discharge from which the cleaving solvent, decylbenzene, is removed by distillation at 85° C. to 90° C. and 0.1 to 0.2 millibars of pressure. This leaves 102 parts of a mixture of 78 percent of diphenylmethane diisocyanates plus 17 percent of 3-nucleus and 5 percent of higher nucleus polyphenyl polymethylene polyisocyanates.

The embodiments of the invention in which an exclusive privilege or property is claimed are defined as follows:

1. A process for the preparation of mixtures of diphenylmethane diisocyanates and polyphenyl polymethylene polyisocyanates comprising the steps of
   A. reacting aniline with an O-alkylcarbamate to form N-phenylurethane;
   B. separating ammonia and other by-products from the N-phenylurethane;
   C. condensing, in the presence of an acid, the resultant N-phenylurethane with formaldehyde or bifunctional compounds having the formula

   $$X—CH_2—X$$

in which X stands for a RO—, RS— or ROCO radical and R denotes an alkyl radical to form mixtures of methylene bis(phenylurethanes) and polymethylene polyphenylurethanes;
   D. cleaving the mixtures of methylene bis(phenylurethanes) and polymethylene polyphenylurethanes at temperatures of 175° C. to 600° C.; and
   E. isolating the mixtures of diphenylmethane diisocyanate and polyphenyl polymethylene polyisocyanates resulting from step D.

2. The process of claim 1 wherein step A is carried out in the presence of a catalyst which is a compound containing one or more cations of metals selected from the group consisting of groups IA, IB, IIA, IIB, IIIA, IIIB, IVA, IVB, VA, VB, VIB, VIIB and VIIIB of the periodic chart.

3. The process according to claim 1 or 2 wherein urea and alcohol are used in addition to the O-alkylcarbamate for the manufacture of the N-phenylurethane with the mole ratio of urea to alcohol being equal to or smaller than 1.

4. The process of claim 1 or 2 wherein the ingredients for the manufacture of the N-phenylurethane are reacted in such quantities that the mole ratio of anline to O-alkylcarbamate to alcohol is 1 to 0.5:20 to 0:100.

5. The process according to claim 3 wherein a maximum of 1.5 urea equivalents, relative to aniline, are used in addition to the O-alkylcarbamate in the manufacture of N-phenylurethane.

6. The process of claim 1 wherein the N-phenylurethane is condensed in a single stage with a compound selected from the group consisting of formaldehyde, acetals having the formula $CH_2(OR)_2$, or acylals having the formula $CH_2(OCOR)_2$, in which R stands for an alkyl radical, in the presence of acids at temperatures of 50° C. to 150° C.

7. The process of claim 1 or 6 wherein sulfuric acid, methane sulfonic acid, trifluoromethane sulfonic acid, or strongly acid organic cation exchangers are used as acids for the condensation of the N-phenylurethanes.

8. The process of claim 1 wherein the mixtures of methylene bis(phenylurethanes) and polymethylene polyphenylurethanes in the liquid phase in a solvent, are cleaved thermally at temperatures of 175° C. to 350° C. in the presence of metals selected from the group consisting of zinc, aluminum, titanium, iron, chromium, cobalt and nickel, as catalysts, which are present in the heterogeneous phase.

9. The process of claim 8 wherein a solvent is used for the thermal cleaving in the liquid phase, the boiling point of which is between that of the 4,4'-diphenyl diisocyanate and that of the separated alcohol.

10. The process of claim 1 or 8 wherein the cleaving catalyst has a large surface area, said catalyst being aluminum or zinc.

11. The process of claim 1 or 8 wherein the mixture of methylene bis(phenylurethanes) and polymethylene polyphenylurethanes is thermally cleaved in the liquid phase, wherein part of the resultant diphenylmethane diisocyanate is removed by distillation together with the solvent and is recycled together with the solvent to a cleaving reactor, and wherein the mixture of the remaining part of the diphenylmethane diisocyanates and polyphenyl polymethylene polyisocyanates is removed as a bottom fraction.

* * * * *

UNITED STATES PATENT AND TRADEMARK OFFICE
CERTIFICATE OF CORRECTION

PATENT NO. : 4,349,484

DATED : September 14, 1982

INVENTOR(S) : FRANZ MERGER ET AL

It is certified that error appears in the above—identified patent and that said Letters Patent is hereby corrected as shown below:

On the first page of patent for bibliographic data add "Foreign Application Priority Data - Oct. 20, 1979, Federal Republic of Germany, Serial No. 29 42 542."

Signed and Sealed this

Twenty-eighth Day of December 1982

[SEAL]

Attest:

GERALD J. MOSSINGHOFF

Attesting Officer

Commissioner of Patents and Trademarks